Figure 1:
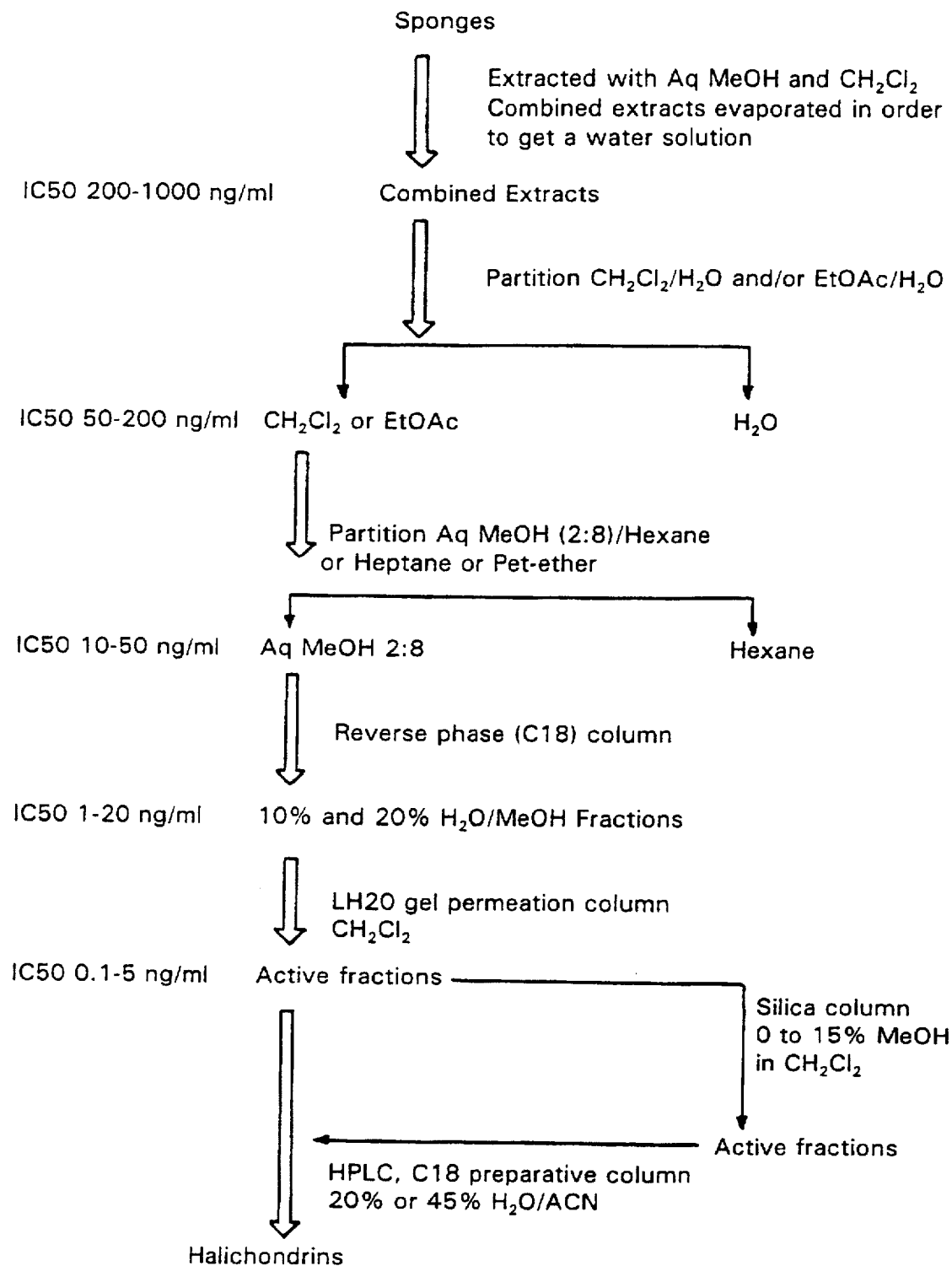

United States Patent [19]
Gravalos et al.

[11] Patent Number: 5,786,492
[45] Date of Patent: Jul. 28, 1998

[54] HALICHONDRINS

[75] Inventors: Dolores G. Gravalos, Madrid, Spain; Robin J. Lake, Christchurch 1, New Zealand; John W. Blunt, Christchurch 1, New Zealand; Murray H. G. Munro, Christchurch 1, New Zealand; Marc S. P. Litaudon, Christchurch 1, New Zealand

[73] Assignee: Pharma Mar, S.A., Madrid, Spain

[21] Appl. No.: 902,364

[22] Filed: Jul. 29, 1997

Related U.S. Application Data

[63] Continuation of Ser. No. 460,407, Jun. 1, 1995, abandoned, which is a continuation of Ser. No. 35,382, Mar. 22, 1993, abandoned.

[30] Foreign Application Priority Data

Mar. 23, 1992 [GB] United Kingdom ............... 9206244

[51] Int. Cl.$^6$ ................ C07D 313/00; C07D 493/22
[52] U.S. Cl. ............................. 549/268; 549/344
[58] Field of Search ..................... 549/268, 344

[56] References Cited

PUBLICATIONS

*J. Med. Chem.* 34(11), pp. 3339–3340; Pettit, 1991.

*Tetrahedron Letters*, 28(30), pp. 3463–3466; Aicher et al; 1987.

*J. Am. Chem. Soc.*, 107(16), pp. 4796–4798; Uemura et al; 1985.

*Pure & Appl. Chem.*, Halichondrins—antitumor polyether macrolides from a marine sponge, vol. 58, No. 5, pp. 701–710; 1986.

*Primary Examiner*—Ba K. Trinh
*Attorney, Agent, or Firm*—Ernest V. Linek; Dike, Bronstein, Roberts & Cushman, LLP

[57] ABSTRACT

Halichondrin derivatives, isolatable from a marine sponge of the Lissodendoryx Sp., have cytotoxic preparations and are of the formula:

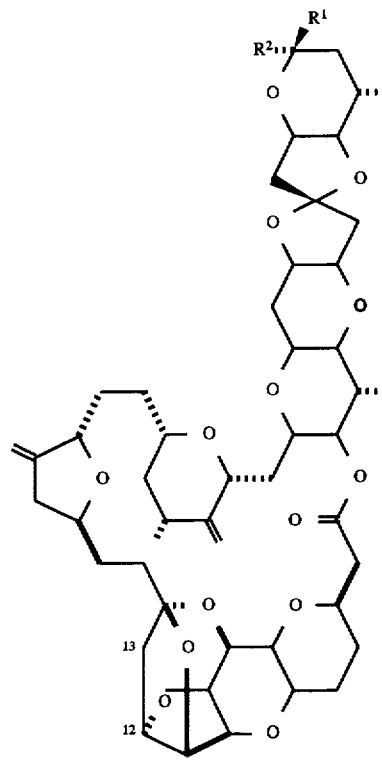

wherein $R^1$ and $R^2$ together form a spiro attached ring system selected from the group consisting of:

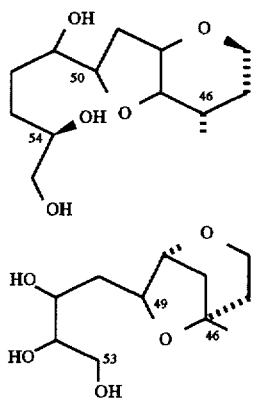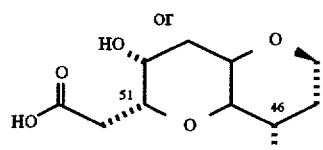
4 Claims, 1 Drawing Sheet

HALICHONDRINS

This application is a continuation of application Ser. No. 08/460.407 filed on Jun. 1, 1995, now abandoned, which is a continuation of application Ser. No. 08/035,382 filed on Mar. 22, 1993, now abandoned.

This invention is concerned with halichondrins isolatable from a marine sponge of Lissodendoryx Sp.

Certain halichondrins, as hereinafter more particularly described, have been isolated from a marine sponge of Lissodendoryx Sp. and have been found to have cytotoxic activity, as evidenced by in vitro tests.

Accordingly, the invention provides halichondrin derivatives of the formula:

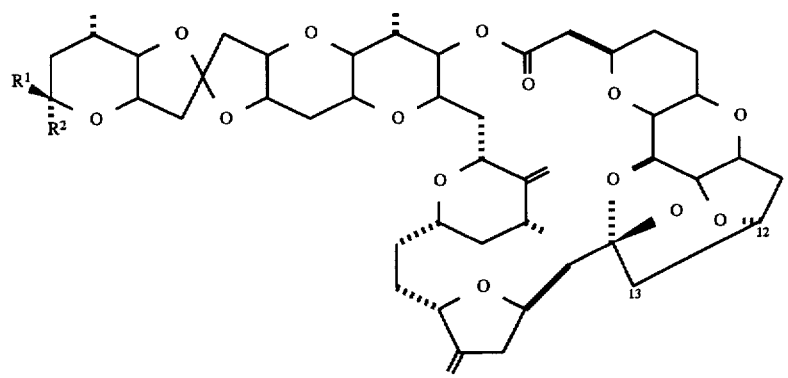

in which $R^1$ and $R^2$ together form a bi- or tricyclic oxygen-containing fused ring system substituted with a hydroxylated alkyl chain and having the formula:

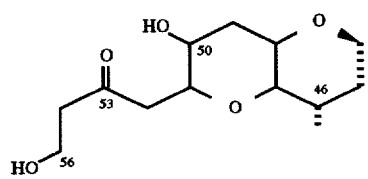

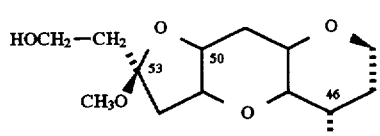

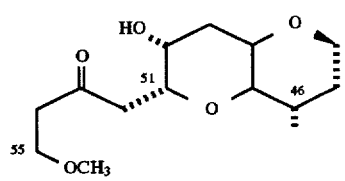

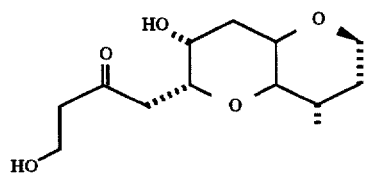

-continued

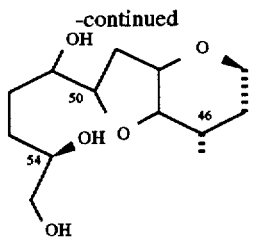

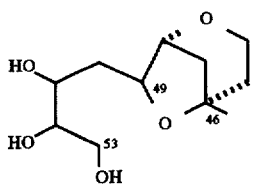

or

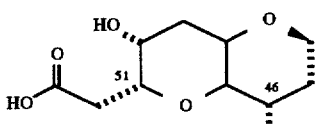

The compounds of the invention, as noted above, possess cytotoxic activity and the invention further provides pharmaceutical compositions containing the above compounds, together with a pharmaceutical carrier or diluent. The invention also provides a method for the preparation of a cytotoxic compound using, as active ingredients, a compound as defined above. Finally, invention provides a cytotoxic method using the compounds of the invention.

The compounds of the invention have been isolated from a sponge of the Lissodendoryx genus which occurs in moderate depths on the shelf off the Kaikoura Peninsula (e.g.

at the position 42° 26.20'S; 173° 44.30'E). In this district it is a sponge of moderate abundance and is found at a depth of approximately 100 m.

Lissodendoryx n.sp. 1 is a Myxillid sponge represented by original collection specimen U228-10, housed within the University of Canterbury, New Zealand, Chemistry Department Collection. The sponge is massive in life forming amorphous mounds up to 50 cm diameter. The surface is lumpy and slightly translucent. The sponge is yellow externally and internally, and exudes mucus on exposure to air. Microscleres are sigmas and arcuate isochelae. Megascleres are acanthostyles and tylotes of one class only. The sponge is found closely associated with a Forcepia sp.

The halichondrins were isolated from the sponge in accordance with the general method shown in the accompanying drawings as described more fully in FIG. 1.

EXTRACTION AND PARTITIONS

The extraction was carried out with about 4 l/kg of 10 to 20% $H_2O$ in MeOH and 4 l/kg of $CH_2CL_2$ in order to get, once the combined extracts were evaporated, about 0.5 to 0.8 liter of an aqueous solution. The use of the minimum amount of methanol eases the first partition.

The first partition gives better results with EtOAc than with $CH_2Cl_2$ (emulsion less of a problem).

The second partition gives better results with hexane or heptane than pet-ether.

During the evaporation of the aqueous methanol, using a rotavopor, some problems occur (bubbles) when the proportion of methanol is around 10%. In order to avoid this problem, it is useful to evaporate small volumes of solvent in large round bottom flasks (200 ml in a 1000 ml flask for example) and it is useful to add some dichloromethane at this stage to make an azetrope with the methanol and finally to spin the flask faster to collapse the bubbles.

The $IC_{50}$ (consequently the number of units) found in the fractions coming from these steps may be considerably affected by the salts or the fats.

Purification by Chromatography

C18

The crude extract (usually several grammes to several ten grammes) is put in methanol solution the day before the C18 chromatography, then an identical volume of distilled water is added before loading the solution onto the column (in order to get a 1/1 $H_2$/MeOH solution). The solution may also be adsorbed on celite and evaporated to give a powder or a slurry to load onto the column.

10 to 20 g of C18 material/g of extract are sufficient. A gradient of MeOH/water to MeOH/$CH_2Cl_2$(1/1) is used for elution. About 25 ml of solvent/g of crude extracts are used for 50, 40 and 30% of water in methanol, about 50 ml/g for 20 and 10% and 20 to 40 ml/g for MeOH 100% and MeOH/$CH_2Cl_2$(1/1).

Sephadex LH20

The permeation gel is put in $CH_2Cl_2$ solution. About 200 to 250 g of Sephadex is used (total volume of 800 ml) for each column (dim 4.5×50 cm), 200 to 800 mg of extract may be loaded onto the column. The less polar halichondrins (LP1, LP2, LP3 and isohomohalichondrin B) came through first associated with a very polar material (probably large polymers which form a film in the vial during the drying), then the polar halichondrins (Hb, HoB, minor 1 and minor 2) are eluted with some fatty acids and a few sterols. Once the column is finished (only 4 or 5×100 ml fractions are sufficient to collect the halichondrins), the Sephadex LH20 is washed using MeOH/$CH_2Cl_2$ 1/1 (100 ml) to remove all the undesired compounds, this may be achieved using a sintered funnel.

Silica

A supplementary step on a silica column may be used before the final purification on HPLC. About 30 times the mass of extract must be used for the silica (∅1.6×115 cm=30 $cm^3$, davisil 35–70 μ form a 50–100 mg weight extract). A gradient from 0 to 5% of MeOH in $CH_2Cl_2$ is used to purify the less polar halichondrins and from 2 to 15% for the polar halichondrins. This supplementary step is particularly useful when some fatty acids or sterols are contained in the fraction. (No further purification was necessary to get LP1 after this step).

HPLC, C19 Preparative Column

UV detection at wavelength 200 nm, the attenuations usually used are 0.64 or 1.28, or 2.56 if the amount of each halichondrin is around 1 to 2 mg/injection.

Characteristic of the column –column+precolumn, 25+5 cm L×21.4 mm ID, 8 μ 60 A particles.

The mobile phase is chosen with respect to the polarity of the compounds. A mixture of 55% ACN in $H_2O$ used for the polar halichondrins (flow rate of 5 ml/min) gives retention times of 17, 22, 23 26 and 40 min for minor 2, minor 1, halichondrin B, homohalichondrin B and isohomohalichondrin B respectively. A mixture of 80% ACN in $H_2O$ used for the less polar compounds gives retention times of 24, 34, 40 and 50 min for isohomohalichondrin B, 1p3, 1p2 and 1p1 respectively.

Not more than 10 mg (400 ∂ loop) is injected in one time. To avoid the conversion of the less polar (LP1 or 3) compounds in isohomohalichondrin B, the sample is dissolved in acetonitrile before the injection rather than methanol. A simple filtration of the sample on cottonwool is sufficient before the injection. In order to get more of minor compounds, the collection of the fractions is carried out as follows:

—for the polar compounds, every 3 or 4 minutes from the solvent peak to the 1st main compound (which is halichondrin B, minor 1 can also be collected separately) and one fraction will be recovered between homohalichondrin B and isohomohalichondrin B.

—for the less polar compounds every 4 or 5 minutes between isohomohalichondrin B and 1p1. Then, when several injections would have been done, the fractions, which present the same retention times, will be combined and reinjected, using the same mobile phase but a smaller attenuation (of the UV detector), in order to detect smaller peaks.

24.5 kg of the original 47 kg has been processed with the isolation of 52.8, 53.5 and 65.8 mg (yield of $5.06×10^{-5}$%, $5.22×10^{-5}$% and $6.31×10^{-5}$% of wet sponge) of halichondrin B, homohalichondrin B and isohomohalichondrin B respectively. Minor compounds have been isolated and the structure of six of them have been established.

The structures of the compounds have been established on the basis of different NMR techniques: $^1H$ NMR, $^{13}C$ NMR, $^1H$—$^1H$ cosy, 1D and 2D TOCSY, HMQC and HMBG, measured on a 300 MHz (except for isohomohalichondrin B, some NMR experiments have been done on a 500 MHz) in $CDCl_3$/Pyridine 0.1%, $CDCl_3$ and $CD_3OD$. All the compounds investigated so far belong to the B series characterised by the absence of hydroxyl groups in position 12 and 13, according to the nomenclature adopted by Uemura. The differences between compounds take place at the terminal part of the molecule (from position 44), the remaining part being unchanged.

ISOHOMOHALICHONDRIN B (ML1 43.3)

Isohomohalichondrin B was obtained as a white amorphous powder; no UV maximum above 210 nm; IR (NaCl pellet) 3450, 1732, 1695 (sh), 1648 cm−1 indicated the presence of hydroxyls, a lactone larger than a five-membered ring as for the previously reported norhalichondrin A, an aliphatic ketone and exomethylenes. The mass spectrometry show $MNa^+$ and $MK^+$ at m/z 1145 and 1161 respectively leading to the molecular weight of 1122. The HRFABMS observed is at m/z 1161.5395 ($MK^+$, calc: 1161.53999; error—0.4 ppm) corresponding to an elemental composition of $C_{61}H_{86}O_{19}$ requiring 19 sites of unsaturation as for homohalichondrin B.

The structure was established mainly on the basis of $^1H$—$^1H$ cosy spectra measured on a 300 MHz instrument in two different solvents: $CD_3OD$ and $CDCl_3$/pyridine-$d_5$ 0.1% and on a 500 MHz instrument in $CDCl_3$/pyridine-$d_5$ 0.1% only. Proton connectivities from C1 to C46 were identical with those of halichondrin B or homohalichondrin B. Otherwise, three spin systems (see table 1 below) are novel in that they have no obvious equivalent in the spectra of any of the halichondrin "B" type molecules.

TABLE 1

| | | $^1H$ chemical shift (CDCl$_3$, in ppm; J in Hz) | COSY correlation |
|---|---|---|---|
| | H47 | 3.27 | |
| 1 | H48 | 3.75 m | 1.84, 2.13 |
| | H49 | 2.13 m | 1.84, 3.52, 3.75 |
| | H49' | 1.84 m | 2.13, 3.52, 3.75 |
| | H50 | 3.52 m | 1.84, 2.13 |
| 2 | H51 | 3.82 m (8.3, 5.2) | 2.62, 2.93 |
| | H52 | 2.93 dd (15.7, 8.3) | 2.62, 3.82 |
| | H52' | 2.62 dd (15.7, 5.2) | 2.93, 3.82 |
| 3 | H54 | 2.74 dt (6.2, <1) | 3.86 |
| | H55 | 3.85 t (6.2) | 2.74 |

Moreover, the signals assigned from H47 to H51 are comparable with those observed in norhalichondrin A and the chemical shift for the proton on C52 and C54 suggested that these protons are adjacent to a carbonyl carbon (see table $^1H$ NMR).

Sixty one carbons were observed in the $^{13}C$ NMR spectrum of isohomohalichondrin B. A HMQC experiment confirmed the presence of 4 methines (CH bearing an O) and 4 methylenes for the "left hand" side chain end (from C47 to C55). A HMBC experiment measured on the 500 MHz supported the sequence C52 to C55 by the observation of long range correlations between the three methylenes 52, 54 and 55 and the carbon at 209.5 ppm as shown diagram 1. Stereochemistry of isohomohalichondrin B was also supported by a NOESY experiment (diagram 2), this showed that carbon 47 and 48, 50 and 51 were all cis (chair conformation), subsequently the hydroxyl group on C50 and the side chain are below the plane.

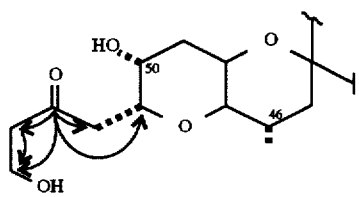

diagram 1: HMBC connectivities

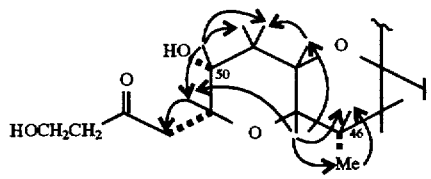

diagram 2: Noesy connectivities

A probable hydrogen bond between the carbonyl 53 and the hydroxyl beared by the carbon 50 explain the difference of the chemical shift of the two protons of the methylene 52 and also of the methylene 54 which appear as a quadruplet (doublet of triplet on the 300 MHz). In fact this quadruplet is a part of a more complicated system observed by modeling. The measurement of the relaxation time of the $CH_2$ 54 and 55 give twice in average the t1 values of the other protons, this could be due to a larger motion of the end side chain of the compound.

(Finally it has been observed, based on the $^1H$ NMR spectra of several samples (in $CDCl_3$), that isohomohalichondrin B may exist in two different conformations in solution. The sharp triplet at δ 3.84 ppm, for some unclear reasons, disappear to give a broad signal, the triple at δ 2.74 ppm being unchanged).

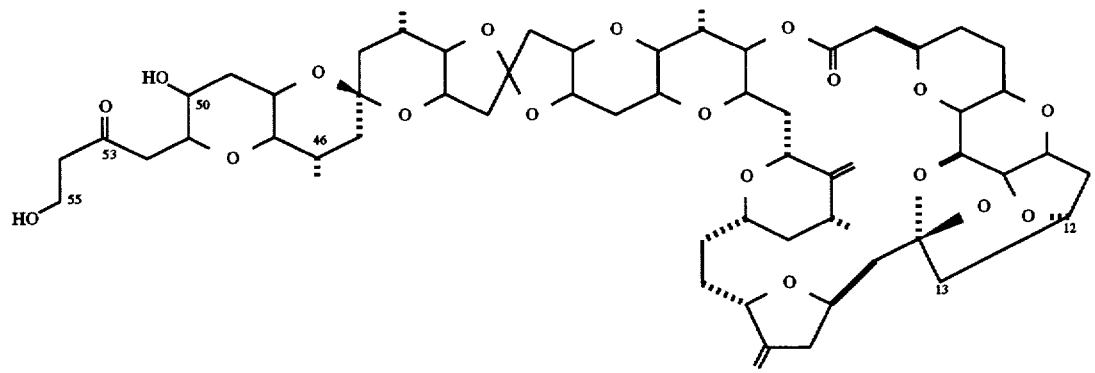

Chemical Transformation

It is interesting to note that this compound, if left in a NMR tube in methanol for a few weeks, transforms in another compound with an acetal carbon a lp1 or lp3 (see less polar halichondrins) or a hemiacetal carbon (in position 53), compound especially characterised by the shift of H47 from 3.27 to 3.13 ppm (in $CD_3OD$) and the disappearance of the three methylenes 52, 54 and 55. This observation has been done by R. Lake and partially reproduced (two third of the sample, exposed to day light at room temperature, was transformed after 12 weeks). Several nOe experiments have been performed, in $CD_3OD$, in order to prove the transformation. The irradiation of the new signal at δ 3.13 ppm (H47) led to the enhancement of two protons at δ3.62 and 4.00 ppm and vice versa, which compared with those of homohalichondrin B, are likely to be H48 and H51 involved in a 6-membered ring attached to a terminal 5-membered ring. Furthermore the irradiation of H51 at d 4.00 ppm led to the enhancement of protons at δ 3.90 and 2.20 ppm (H50 and $CH_2$52 respectively). A HMQC experiment has been performed and, according to the chemical shifts of the carbon given by Uemura for homohalichondrin A, agree fully with a "homotype halichondrin" structure (see table 2 below).

TABLE 2

Chemical shifts (in ppm) of the methines (and the methylenes 52 and 55) of the terminal moiety of:

|  | New compound ($CD_3OD$) | Homohalichondrin A ($CD_3OD$) | Lp1 ($CDCl_3$) |
| --- | --- | --- | --- |
| C47 | 75.2 | 74.5 | 74.2 |
| C48 | 64.9 | 65.2 | 63.3 |
| C50 | 74.8* | 75.4 | 73.0 |
| C51 | 79.0 | 78.4 | 77.7 |
| C52 | 45.5 |  | 45.3 |
| C55 | 59.5 | 65.1 | 58.3 |

*overlapping with other carbon

LP1, ML1 154.8 and ML1 173.13

Lp1 is the less polar compound ever isolated of the halichondrin family. Around 12 mg of this compound have been isolated from a silica column and around 3 mg have been isolated from the final HPLC step, it is quite unstable and give isohomohalichondrin B by chemical transformation. This transformation can occur during the process of purification or on the mass spectrometry matrice or in the NMR tube within 4 or 5 days. The low-resolution FABMS spectrum (NOBA+KCL) show two main peaks at m/z 1175.4 ($MK^+$) and 1159.5 ($MNa^+$) and lead to the mass of 1136. High resolution FABMS of the most abundant peak after transformation is 1297.57984 (mass+NOBA+K–$OCH_3$, calculated for C68H92NO21K, 1297.5755 ppm). On this basis the molecular formula is C62H88O19.

The main differences with the precedent compound on the $^1H$ NMR are the absence of the two triplets at δ 2.71 and 3.86 ppm, $CH_2$54 and 55 respectively but the presence of two broad doublets at δ 3.1 and 3.96 ppm (1H each, H47 and H51 respectively) and a sharp singlet at δ 3.23 ppm (3H, $CH_3O$ 53). The chemical shift of H47 is very specific as its position distinguishes the 3 main types of halichondrin. In the "nor" series, H47 is at δ 3.35 ppm while in the "halichondrin" series it is at δ 3.56 ppm. In our case, 3.1 ppm is in favor of a "homohalichondrin type" molecule ending with a five-membered ring attached to a six-membered ring.

HMQC and $^{13}C$ NMR, realised before and after the transformation, have been the turning point to find out the structure. The ketal carbon 53 at δ 109.3 ppm disappear to give the ketone at δ 209.5 ppm. The two methylenes 52 and 54 were at δ 45.2 and 35.5 ppm respectively before the transformation, chemical shifts comparable with those of C13 and C15 (48.3 and 34.4 ppm respectively) which are involved in a similar manner regarding a ketal carbon.

All these data allowed to propose the following structure (figure below). The $^1H$ NMR and $^{13}C$ NMR tables are given at the end of the report.

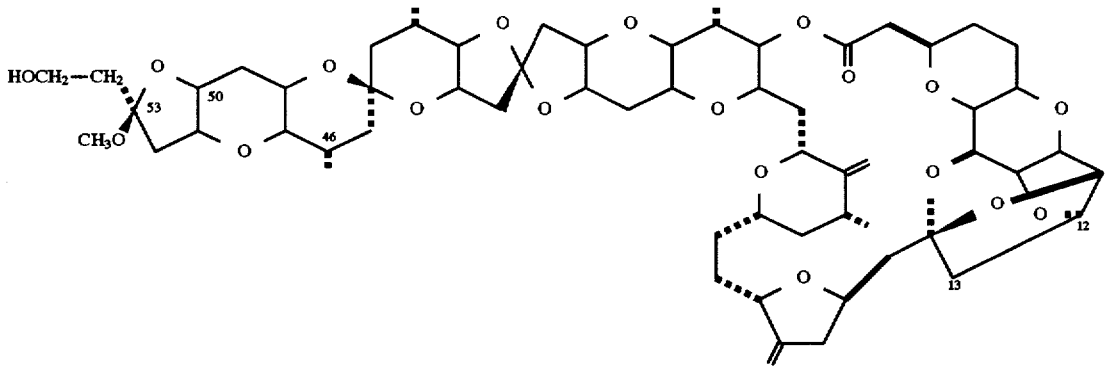

Finally a thin layer chromatography has been realised in order to compare the polarity of the different compounds (silica, eluent methanol 5% in dichloromethane). This one show clearly two spots for the sample containing isohomohalichondrin B and the transformed compound; this last one, having the same rf as lp1, is likely to be lp1.

LESS POLAR HALICHONDRINS

These compounds are, based on their retention times on a HPLC preparative C-18 column, less polar than isohomohalichondrin B. They all have only one hydroxyl group.

Several nOe experiments have been performed on lp1 and agree with the proposed chair conformation for the terminal rings (from C44); this has been observed for isohomohalichondrin B where H 47, 48, 50 and 51 are all in a cis position. The irradiation of H 47 led of the enhancement of the 4 signals H 46, $CH_3$ 46, H 48 and H 51 whereas irradiation of the signal at δ 3.96 ppm (H 51) led to the enhancement of only 2 signals at δ 2.24 and 3.08 ppm ($CH_3$52 and H 47 respectively). Finally, the irradiation of H 50 (at δ 3.88 ppm) lead to the enhancement of signals at δ

3.96 ppm (H 51), 2.20 ppm (H49) and of the methoxyl at δ 3.23 ppm, allowing us to determine the relative configuration of the carbon 53 (S). The irradiation of the methoxyl, which give enhancements of H 50 and 52, confirm the proposed configuration.

The acetal hydrolysis and consequently the formation of the ketone could be explained by loss of the methoxyl, after attack of a base B⁻, leading to a carbocation and opening of the ring according to the subsequent scheme. The same reaction occur also on 1p3. The reverse reaction, although much slower, has been realised on a sample of isohomohalichondrin B in methanol.

Terminal part of LP2

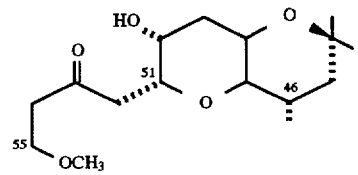

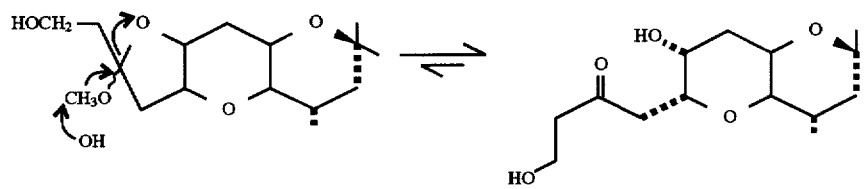

CONCLUDING REMARKS

The problem is now to determine which compound is the natural compound. It has been observed that the transformation of 1p1 (or 1p3) in isohomohalichondrin B is relatively fast whereas the reverse reaction is much slower, this implying a much more stability of isohomohalichondrin B. However the existence of 1p3 will tend to prove that the reverse reaction (iso B→1p1+1p3) occur during the process of extraction or purification, depending of the conditions. The probable hypothesis to explain these observations is to consider a relatively unstable compound with an acetal or a hemiacetal carbon in position 53 at the origine of the formation of isohomohalichondrin B, which would give back, in slight amount, 1p1 and 1p3. The discovery of a compound with a hemiacetal carbon in position 53 has not been proved yet although some other minor compounds have been found.

LP2; ML1 200.5

Only 0.7 mg of this compound have been isolated. The HRFABMS observed is at m/z 1137.6018 (MH⁺, calc: 1137.5998; error 1.8 ppm) corresponding to an elemental composition of $C_{62}H_{89}O_{19}$. On examination of the proton NMR spectrum of this compound, it has been found that it is very similar to the one of isohomohalichondrin B but the presence of a sharp singlet at δ 3.34 ppm (3 protons) and the shift of the triplet from 3.85 ppm to 3.62 ppm are in favor of a methoxyl attached to the methylene 55 instead of an hydroxyl in the case of isohomohalichondrin B. However nOe enhancements are observed, after irradiation of the methylene in position 55, of the terminal methoxyl and of both methylenes 52 and 54, which support the proposed sequence and implicate a probable hydrogen bond between the carbonyl and the hydroxyl in position 50 as shown figure below.

A 2D TOCSY experiment has been performed and the data are fully in agreement with the proposed structure, especially correlations between the two methylenes 54 and 55, the two protons of methylene 52 and correlations involved in the spin system from H47 to H50 are well resolved.

LP3 (ISOMER OF LP1); ML1 173.11

Only 1.5 mg of this compound have been isolated. As 1p1, this compound is very unstable and transforms very quickly to give isohomohalichondrin B. Isohomohalichondrin B has been identified after examination of the ¹H NMR in CDCl₃, especially characterised with the two sharp triplets at d 2.74 and 3.85 ppm (CH₂54 and 55 respectively). The ¹H NMR of 1p3, except a different chemical shift for the methoxyl on C 53 at δ 3.40 ppm and possibly of the proton H51 at δ 3.91 ppm (3.23 ppm and 3.96 ppm respectively in 1p1), does not display any difference with the spectrum of 1p1. These data imply the configuration R for the carbon 53; consequently 1p3 would be the enantiomer of 1p1.

OTHER LESS POLAR HALICHONDRINS

Two, may be three, other less polar compounds have been isolated. The ¹H NMR of the fraction ML1 173.7, which eluted from C18 just after isohomohalichondrin B (the chromatogram displays 2 peaks), show one signal at δ 3.08 ppm as 1p1 (probably H47) but no methoxyl. Furthermore the methyl region looks like more homohalichondrin B than isohomohalichondrin B, which is in favor of a "homotype" halichondrin with, possibly, a hydroxyl in position 53. The ¹H NMR of the fraction ML1 173.8 (which contain 1p1, iso B and 2 other compounds based on the chromatogram) show 2 signals around 3.1 ppm indicating that one of these signals belong to a compound different from 1p1 (3.09 ppm being probably H47 of 1p1). A similar signal, at δ 3.11 ppm, is found again in the NMR spectrum of the samples ML1 196.7 and RT1 158.8, which do not dysplay any methoxyl.

POLAR HALICHONDRINS

These compounds are more polar than halichondrin B, having shorter retention times on a HPLC preparative C-18 column. Two minor compounds have been isolated so far (minor 1 and 2), both are fully described although some uncertainties remains.

MINOR 1, ML1 138.2

This compound has similar polarity to halichondrin B (the chromatogram displays usually a very small peak before halichondrin B); aroud 7 mg have been purified and isolated. The HRFABMS observed is at m/z 1163.5553 (MK$^+$, calc: 1163.5550; error—0.3 ppm) corresponding to an elemental composition of $C_{61}H_{88}O_{19}$ (one more $CH_2$ compared to halichondrin B).

The carefull examination of the HMQC spectrum point out the similarity with the one of halichondrin B except some little differences (see table 3).

TABLE 3 chemical shifts in ppm, $^1H$ and $^{13}C$ NMR in $CDCl_3$

|  | Halichondrin B | Minor 1 |
|---|---|---|
| C/H47 | 80.2/3.61 | 79.3/3.52 |
| C/H48 | 71.7/4.05 | 71.6/4.05 |
| C/H$_2$49 | 35.9/1.90, 2.32 | 32/1.95, 2.10 |
| C/H50 | 79.0/4.08 | 80.9/4.05 |
| C/H51 | 73.0/3.80 | 72.7/3.85 |
| C/H53 | 70.4/4.02 |  |
| C/H$_2$54 | 66.9/3.54, 3.61 |  |
| C/H54 |  | 72.3/3.70 |
| C/H$_2$55 |  | 66.8/3.45, 3.63 |

Except these differences, all the other correlations are identical to halichondrin B. The $^{13}C$ NMR spectrum shows 61 carbons and again is very close to halichondrin B, except an extra carbon supposed to be a $CH_2$ and having a chemical shift of 31.1 ppm.

These data are in favor of a terminal 5-membered ring as it has been observed in halichondrin B following by a side chain which would contain one more $CH_2$. As the cosy spectrum shows a correlation between 3.45 and 3.70 ppm (H55 and H54 respectively), we can assume that the side chain ends by —CHOH—CH$_2$OH. Three different possibilities remain regarding the position of the extra methylene. The examination of cross sections for 2D TOCSY spectra, realised with 2 different mixing times, removed the ambiguity. Taking the trace at δ 3.70 ppm (which is assigned unambiguously to H 54), from the "20 ms 2DTOCSY", three correlations were seen at δ 3.45 (triplet) and 3.63 ppm (CH$_2$ 55) and at δ 1.6 ppm (broad signal, CH$_2$ 53). Taking the same trace from the "100 ms 2D TOCSY", supplementary correlations were observed at δ 1.4 ppm (broad signal, CH$_2$ 52) and at d 3.85 ppm (doublet, CH 51) and indicated that these two signals were placed further from the original one. Finally from the trace at δ 4.05 ppm (CH 50) a correlation was observed at δ 3.85 ppm (doublet, CH 51) while correlations at δ 1.4 and 1.6 ppm were very weak, which supported the following sequence —CHO$_{(50)}$—CHOH$_{(51)}$—CH$_2$(52)—. A large coupling constant (doublet, J=11.1 Hz) of the signal at δ 3.85 ppm is in agreement with this proposition (otherwise, if this methine was placed between the two methylenes, we would have expected a triplet). A HMBC experiment (JNXH=4.5 Hz) has been performed but failed to confirm or infirm the proposed side chain.

The proposed terminal moiety is shown below.

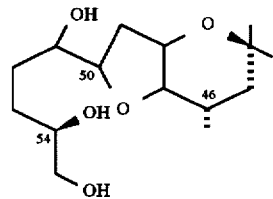

Minor 1

(In order to determine the chiralite of the methine carbons some nOe differences spectra will be run).

MINOR 2, ML1 200.4

This compound is the more polar isolated so far. Only 0.9 mg has been isolated. A low resolution FAB mass spectrometry has been realised and gave two peaks at m/z 1097 and 1135 (MH$^+$ and MK$^+$ respectively). The HRFABMS observed is at m/z 1097.5690 (MH$^+$, calc: 1097.5685 error 0.4 ppm) corresponding to an elemental composition of $C_{59}H_{85}O_{19}$.

The $^1H$ NMR spectrum shows some very unusual features compared to halichondrin B or minor 1. In the methyl region, only three doublets are present around 1 ppm, a fourth methyl appears to be a singlet at 67 1.35 ppm indicating the probable presence of an oxygene bearing carbon instead of the usually seen methine on a position. Two doublets (at δ 2.86 ppm, J=11.2 Hz and δ 3.73 ppm, J=4.9 Hz) seems also characteristic of this compound.

The carefull examination of a 2D TOCSY (run with a 100 ms mixing time) and a HMQC experiment allowed us to find out the main part of the compound, unchanged until carbon 44 compared to the halichondrin skeleton (except a small shift for H 40 at δ 4.18 ppm usually 4.0 ppm). However the HMQC experiment show six new carbons in the "carbon bearing oxygen" region and four (including the new methyl) in the methylene region. Among these, one methylene is particularly deshielded (at δ 54.2 ppm) considering the chemical shifts of the 2 protons (1.86 and 2.11 ppm), suggesting that it is close to a ketal carbon with a supplementary b effect of an oxygen atom; the 2 protons involved in the second methylene (at δ 37 ppm) have a very different chemical shift (1.52 and 2.86 ppm), the proton at δ 2.86 ppm could be located close to an oxygen atom. According to the chemical shifts of protons and carbons (and compared with those of halichondrin B and minor 1) and based on the results obtained from the 2D TOCSY experiment we can proposed the following fragment: HOCH$_2$—C$_{(52)}$HOH—CHOH—CH$_2$—C$_{(49)}$HO—CHO—CH$_2$—. In addition we assume that the methine 49 belong to a 5-membered ring (according to the chemical shift of C49 at 81.7 ppm almost identical to the one of halichondrin B or minor 1).

A HMBC experiment has been performed (JNXH=6 Hz) and give the very usefull following informations. Firstly correlations between the methyl at δ 1.35 ppm and 3 carbons at δ 36.8, 52.4 and 80.2 ppm (C 47, 45 and 46 respectively) secondly 2 supplementary correlations with the carbon at δ 80.2 ppm and protons at δ 4.28 (H 48) and 1.88 (H49) ppm. These correlations are shown below.

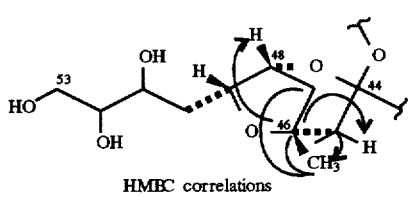

HMBC correlations

NOe experiments (shown above) have been carried out and are in full agreement with a terminal moiety constituted with a 5-membered ring attached to a 6-membered ring (H48 and H49 are in cis position and imply a boat conformation for the 6-membered ring). The enhancements are particularly strong between H48 and both protons of the $CH_2$ 47 and, H48 and H49 whereas between one proton of the methylene 47 (at δ 1.5 ppm) and H49 is less intense.

This unusual arrangement tends to draw nearer one proton of the $CH_2$ 47 and the oxygen atom beared by carbon 44 and this could explain the very deshielded value (at δ 2.86 ppm).

All the precedent informations allow us to propose the following structure for minor 2.

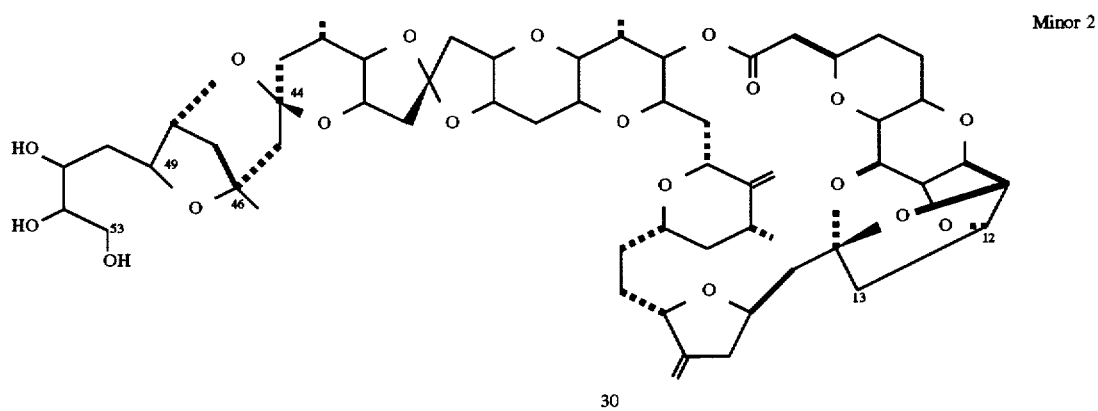

Minor 2

OTHER HALICHONDRINS

NORHALICHONDRIN B, ML1 201.4

Only 0.6 mg of this compound has been isolated. The polarity of this compound is not clear, although it seems a little bit more polar than isohomohalichondrin B based on a silica tlc. The HRFABMS observed is at m/z 1095.5574 (MH$^+$, calc: 1095.5529; error 4.1 ppm) corresponding to an elemental composition of $C_{59}H_{83}O_{19}$.

$^1$H NMR, HMQC, 2D TOCSY and nOe experiments have been performed on this sample. All these experiments allow us to determine the terminal part of the molecule conclusively. This one is constituted with a 6-membered ring, as isohomohalichondrin B, with a $CH_2$—COOH terminal attached on position 51 (the methylene 52 is at δ 260/289 ppm). The chemical shifts of the protons belonging to this last ring present some very small differences with iso B: H47, 48, 50, 51 and $CH_2$49 have a δ at 3.37, 3.81, 3.60, 3.80 and 1.87/2.18 ppm respectively (3.25, 3.75, 3.52, 3.82 and 1.84/2.13 ppm in isohomohalichondrin B). It is interesting to note that the 2 protons of the methylene 52 are non equivalent, probably due to a hydrogen bond between the hydroxyl in position 50 and the CO of the carboxylic acid. This non equivalence disappears when methanol is used as the solvant ($CH_2$ 52 at δ 2.47 ppm, see Uemura's article). NOe experiments support the proposed terminal part; enhancement of H47 after irradiation of H51+H48 and vice versa, enhancement of H51 and H52' after irradiation of H52 at δ 2.61 ppm, enhancement of H51 and H49 after irradiation of H50.

An IR spectrum has been performed and has indicated the presence of hydroxyls (3470 cm$^{-1}$), a lactone larger than 5-membered ring (1735 cm$^{-1}$) and a carboxyl (shoulder on the previous one around 1700 cm$^{-1}$). The terminal part of norhalichondrin B is shown figure below.

Terminal Part of Norhalichondrin B

ML1 206.5 and 206.6 (0.5 and 0.6 mg respectively)

These samples, which are the result of the collect of fractions coming from after homohalichondrin B and before isohomohalichondrin B on HPLC, contains new compounds. We can observed on the $^1$H NMR of the first one an unusual proton at δ 5.75 ppm, which could be attached to an acetal or a hemiacetal carbon (see ref Joc 1990, 55, 863–870). Two new protons at δ 5.9 and 6.4 ppm appeared on the $^1$H NMR of the second sample; one is probably attached to an acetal carbon as we can obseved a methoxyl at δ 3.42 ppm.

RT1 158.2 and 158.6

The first sample contains probably some polar halichondrins (more polar than minor 2), the second one contains some intermediate polar halichondrins (between homohalichondrin B and isohomohalichondrin B).

BIOLOGICAL STUDIES

Most of the compounds have been submitted to the antitumor P388 bioassay. The activities against P388 cell line are reported below.

| compound and reference | IC$_{50}$ (ng/ml) | conc |
| --- | --- | --- |
| LP1, ML1 154.8 | <0.097 | 0.001 |
| | 0.1 | 0.00001 |
| | 0.13 | 0.0001 |
| LP1, ML1 173.13 | <0.09 | 0.001 |
| | 0.05 | 0.0001 |
| Iso B, JH1 59.1 | 0.18 | 0.001 |
| | <0.97 | 0.01 |
| Hali B, ML1 134.4 | 0.78 | 0.0001 |
| | 1.58 | 0.001 |
| ML1 134.4, other day | <0.09 | 0.001 |
| Minor1, ML1 138.2 | 0.79 | 0.001 |
| | 1.9 | 0.01 |
| Minor2, ML1 200.4 | <0.9 | 0.01 |
| | 0.4 | 0.001 |
| LP2, ML1 200.5 | 10.0 | 0.001 |

The results of the antitumor P388 bioassay point out the high efficiency of most of the compounds belonging to the B series.

Isohomohalichondrin B exhibited a strong cytotoxic activity against the murine leukaemia cell (P388 cell line), exceeding that for halichondrin B and homohalichondirn B (IC50: 0.8, 6.7 and 6.4 ng/ml respectively).

| | IC50 (ng/ml) | | |
| --- | --- | --- | --- |
| | P388 | A-549 | HT-20 |
| Isohomohalichondrin B | 0.8 | 1.1 | 1.4 |

TABLE 1

$^1$H NMR DATA OF LP1 (ML1 154.8) AND ISOHOMOHALICHONDRIN B (ML1 43.3), (300 MHz in CDCl$_3$, δ in ppm).

| n° PROTON | LP1 | Isohomo |
| --- | --- | --- |
| H2 | 2.35 | 2.36 |
| H2 | 2.59 | 2.61 |
| H3 | 3.87 | 3.89 |
| H4 | 1.72 | 1.75 |
| H4 | 1.37 | 1.38 |
| H5 | 1.39 | 1.41 |
| H5 | 2.10 | 2.12 |
| H6 | 4.32 | 4.35 |
| H7 | 2.94 | 2.95 |
| H8 | 4.32 | 4.33 |
| H9 | 4.04 | 4.06 |
| H10 | 4.19 | 4.22 |
| H11 | 4.58 | 4.60 |
| H12 | 4.69 | 4.70 |
| H13 | 1.96 | 1.95 |
| H13 | 2.15 | 2.16 |
| H15 | 2.18* | 2.18* |
| H15 | 1.62* | 1.62* |
| H16 | 2.16* | 2.16* |
| H16 | 1.42* | 1.42* |
| H17 | 4.09 | 4.10 |
| H18 | 2.26 | 2.27 |
| H18 | 2.80 | 2.80 |
| C19—CH2 | 4.99 | 5.01 |
| C19—CH2 | 4.91 | 4.93 |
| H20 | 4.37 | 4.39 |
| H21 | 1.42 | 1.42 |
| H21 | 1.90 | 1.90 |
| H22 | 1.61 | 1.62 |
| H22 | 1.61 | 1.62 |
| H23 | 3.54 | 3.55 |
| H24 | 1.05 | 1.05 |
| H24 | 1.69 | 1.72 |

TABLE 1-continued $^1$H NMR DATA OF LP1 (ML1 154.8) AND ISOHOMOHALICHONDRIN B (ML1 43.3), (300 MHz in CDCl$_3$, δ in ppm).

| n° PROTON | LP1 | Isohomo |
| --- | --- | --- |
| H25 | 2.22 | 2.23 |
| C25—CH3 | 1.07 | 1.07 |
| C26—CH2 | 4.80 | 4.83 |
| C26—CH2 | 4.75 | 4.78 |
| H27 | 3.52 | 3.56 |
| H28 | 2.00 | 2.01 |
| H28 | 1.92 | 1.95 |
| H29 | 4.19 | 4.22 |
| H30 | 4.65 | 4.66 |
| H31 | 2.03 | 2.03 |
| C31—CH3 | 0.99 | 1.00 |
| H32 | 3.18 | 3.20 |
| H33 | 3.79 | 3.84 |
| H34 | 1.78 | 1.81 |
| H34 | 2.14 | 2.16 |
| H35 | 4.11 | 4.12 |
| H36 | 4.11 | 4.12 |
| H37 | 2.35 | 2.37 |
| H37 | 1.90 | 1.92 |
| H39 | 2.20 | 2.22 |
| H39 | 2.20 | 2.22 |
| H40 | 3.88 | 3.94 |
| H41 | 3.58 | 3.64 |
| H42 | 2.26 | 2.29 |
| C42—CH3 | 0.93 | 0.95 |
| H43 | 1.63* | 1.55* |
| H43 | 1.35* | 1.33* |
| H45 | 1.72* | 1.49* |
| H45 | 1.40* | 1.52* |
| H46 | 2.20 | 2.18 |
| C46—CH3 | 0.91 | 0.90 |
| H47 | 3.08 | 3.25 |
| H48 | 3.59 | 3.75 |
| H49 | 2.24 | 2.13 |
| H49 | 1.96 | 1.84 |
| H50 | 3.87 | 3.52 |
| H51 | 3.96 | 3.82 |
| H52 | 2.24 | 2.93 |
| H52 | 2.24 | 2.62 |
| C52—OCH3 | 3.23 | |
| H54 | 1.72* | 2.74 |
| H54 | 2.30* | 2.74 |
| H55 | 3.79 | 3.86 |
| H55 | 3.68 | 3.86 |

*Assignments are tentative

TABLE 2

$^{13}$C NMR DATA OF LP1 (ML1 154.8) AND ISOHOMOHALICHONDRIN B (ML1 43.3) (75 MHz in CDCl$_3$, δ in ppm).

| n° CARBON | LP1 | Isohomo |
| --- | --- | --- |
| C1 | 171.2 | 171.1 |
| C2 | 40.4 | 40.4 |
| C3 | 73.7 | 73.6 |
| C4 | 30.7 | 30.6 |
| C5 | 30.0 | 30.0 |
| C6 | 68.2 | 68.2 |
| C7 | 77.7 | 77.6 |
| C8 | 74.3 | 74.3 |
| C9 | 73.8 | 73.8 |
| C10 | 76.5 | 76.5 |
| C11 | 82.1 | 82.1 |
| C12 | 81.1 | 81.0 |

TABLE 2-continued

13C NMR DATA OF LP1 (ML1 154.8) AND ISOHOMOHALICHONDRIN B (ML1 43.3) (75 MHz in CDCl₃, δ in ppm).

| n° CARBON | LP1 | Isohomo |
|---|---|---|
| C13 | 48.3 | 48.3 |
| C14 | 110.1 | 110.0 |
| C15 | 34.4 | 34.4 |
| C16 | 28.1 | 28.1 |
| C17 | 75.4 | 75.3 |
| C18 | 38.7 | 38.7 |
| C19 | 151.6 | 151.7 |
| C19=CH2 | 104.5 | 104.4 |
| C20 | 75.3 | 75.3 |
| C21 | 29.4 | 29.3 |
| C22 | 32.0 | 32.0 |
| C23 | 74.8 | 74.8 |
| C24 | 43.4 | 43.3 |
| C25 | 35.9 | 35.9 |
| C25=CH3 | 18.0 | 18.0 |
| C26 | 151.7 | 151.5 |
| C26=CH2 | 104.2 | 104.1 |
| C27 | 73.5 | 73.5 |
| C28 | 36.9 | 36.9 |
| C29 | 71.2 | 71.1 |
| C30 | 77.2 | 77.2 |
| C31 | 36.5 | 36.5 |
| C31=CH3 | 15.0 | 15.0 |
| C32 | 77.5 | 77.5 |
| C33 | 66.4 | 66.4 |
| C34 | 29.0 | 29.0 |
| C35 | 75.0 | 75.1 |
| C36 | 76.3 | 76.2 |
| C37 | 43.4 | 43.3 |
| C38 | 112.4 | 112.4 |
| C39 | 42.6 | 42.5 |
| C40 | 70.9 | 71.2 |
| C41 | 79.4 | 79.0 |
| C42 | 25.6 | 25.6 |
| C42=CH3 | 17.6 | 17.5 |

TABLE 3

1H NMR DATA OF LP2 (ML1 200.5) AND ISOHOMOHALICHONDRIN B (ML1 43.3), (300 MHz in CDCl₃, δ in ppm).

| n° PROTON | LP2 | Isohomo |
|---|---|---|
| H34 | 1.80 | 1.81 |
| H34 | 2.15 | 2.16 |
| H35 | 4.12 | 4.12 |
| H36 | 4.12 | 4.12 |
| H37 | 2.37 | 2.37 |
| H37 | 1.92 | 1.92 |
| H39 | 2.22 | 2.22 |
| H39 | 2.22 | 2.22 |
| H40 | 3.93 | 3.94 |
| H41 | 3.64 | 3.64 |
| H42 | 2.29 | 2.29 |
| C42—CH3 | 0.95 | 0.95 |
| H43 | 1.55* | 1.55* |
| H43 | 1.33* | 1.33* |
| H45 | 1.49* | 1.49* |
| H45 | 1.52* | 1.52* |
| H46 | 2.18 | 2.18 |
| C46—CH3 | 0.90 | 0.90 |
| H47 | 3.23 | 3.25 |
| H48 | 3.73 | 3.75 |
| H49 | 2.12 | 2.13 |
| H49 | 1.84 | 1.84 |
| H50 | 3.52 | 3.52 |
| H51 | 3.82 | 3.82 |
| H52 | 2.90 | 2.93 |
| H52 | 2.64 | 2.62 |

TABLE 3-continued

1H NMR DATA OF LP2 (ML1 200.5) AND ISOHOMOHALICHONDRIN B (ML1 43.3), (300 MHz in CDCl₃, δ in ppm).

| n° PROTON | LP2 | Isohomo |
|---|---|---|
| H54 | 2.75 | 2.74 |
| H54 | 2.75 | 2.74 |
| H55 | 3.64 | 3.86 |
| H55 | 3.64 | 3.86 |
| C55—OCH3 | 3.34 | |

*Assignments are tentative

TABLE 4

1H NMR DATA OF HALICHONDRIN B (ML1 135.5) AND MINOR 1 (ML1 138.2), (300 MHz in CDCl₃, δ in ppm).

| n° PROTON | Hali B | Minor 1 |
|---|---|---|
| H2 | 2.35 | 2.35 |
| H2 | 2.60 | 2.60 |
| H3 | 3.86 | 3.88 |
| H4 | 1.75 | 1.75 |
| H4 | 1.37 | 1.38 |
| H5 | 1.35 | 1.41 |
| H5 | 2.08 | 2.11 |
| H6 | 4.34 | 4.33 |
| H7 | 2.94 | 2.95 |
| H8 | 4.33 | 4.33 |
| H9 | 4.04 | 4.05 |
| H10 | 4.20 | 4.20 |
| H11 | 4.60 | 4.60 |
| H12 | 4.68 | 4.69 |
| H13 | 1.94 | 1.95 |
| H13 | 2.15 | 2.17 |
| H15 | 2.18 | 2.18* |
| H15 | 1.62 | 1.62* |
| H16 | 2.16 | 2.16* |
| H16 | 1.42 | 1.42* |
| H17 | 4.10 | 4.10 |
| H18 | 2.26 | 2.27 |
| H18 | 2.80 | 2.80 |
| C19—CH2 | 4.98 | 5.00 |
| C19—CH2 | 4.92 | 4.92 |
| H20 | 4.37 | 4.39 |
| H21 | 1.40 | 1.41 |
| H21 | 1.88 | 1.90 |
| H22 | 1.60 | 1.62 |
| H22 | 1.60 | 1.62 |
| H23 | 3.53 | 3.54 |
| H24 | 1.04 | 1.04 |
| H24 | 1.70 | 1.72 |
| H25 | 2.20 | 2.23 |
| C25—CH3 | 1.07 | 1.06 |
| C26—CH2 | 4.81 | 4.80 |
| C26—CH2 | 4.77 | 4.75 |
| H27 | 3.54 | 3.53 |
| H28 | 2.02 | 2.00 |
| H28 | 1.94 | 1.95 |
| H29 | 4.21 | 4.21 |
| H30 | 4.63 | 4.66 |
| H31 | 2.04 | 2.03 |
| C31—CH3 | 0.99 | 1.00 |
| H32 | 3.18 | 3.19 |
| H33 | 3.80 | 3.81 |
| H34 | 1.79 | 1.80 |
| H34 | 2.13 | 2.13 |
| H35 | 4.10 | 4.10 |
| H36 | 4.10 | 4.10 |
| H37 | 2.35 | 2.35 |
| H37 | 1.92 | 1.90 |
| H39 | 2.24 | 2.24 |
| H39 | 2.24 | 2.24 |
| H40 | 4.00 | 4.03 |
| H41 | 3.63 | 3.64 |

TABLE 4-continued

$^1$H NMR DATA OF HALICHONDRIN B (ML1 135.5) AND MINOR 1 (ML1 138.2), (300 MHz in CDCl$_3$, δ in ppm).

| n° PROTON | Hali B | Minor 1 |
|---|---|---|
| H42 | 2.23 | 2.24 |
| C42—CH3 | 0.94 | 0.94 |
| H43 | 1.52 | 1.53* |
| H43 | 1.29 | 1.30* |
| H45 | 1.50 | 1.49* |
| H45 | 1.42 | 1.42* |
| H46 | 2.35 | 2.36 |
| C46—CH3 | 0.99 | 1.00 |
| H47 | 3.61 | 3.52 |
| H48 | 4.05 | 4.05 |
| H49 | 2.32 | 2.10 |
| H49 | 1.90 | 1.95 |
| H50 | 4.08 | 4.05 |
| H51 | 3.80 | 3.82 |
| H52 | 1.62 | |
| H52 | 1.79 | |
| H53 | 4.02 | |
| H53 | | |
| H54 | 3.54 | 3.70 |
| H54 | 3.61 | |
| H55 | | 3.45 |
| H55 | | 3.63 |

*Assignments are tentative

TABLE 5

$^{13}$C NMR DATA OF HALICHONDRIN B (ML1 135.5) AND MINOR 1 (ML1 138.2) (75 MHz in CDCl$_3$, δ in ppm).

| n° CARBON | Hali B | Minor 1 |
|---|---|---|
| C1 | 171.2 | 171.2 |
| C2 | 40.4 | 40.4 |
| C3 | 73.7 | 73.7 |
| C4 | 30.7 | 30.7 |
| C5 | 30.0 | 30.0 |
| C6 | 68.2 | 68.2 |
| C7 | 77.7 | 77.7 |
| C8 | 74.3 | 74.3 |
| C9 | 73.8 | 73.8 |
| C10 | 76.5 | 76.6 |
| C11 | 82.1 | 82.1 |
| C12 | 81.1 | 81.1 |
| C13 | 48.3 | 48.3 |
| C14 | 110.1 | 110.1 |
| C15 | 34.4 | 34.4 |
| C16 | 28.2 | 28.2 |
| C17 | 75.5 | 75.5 |
| C18 | 38.7 | 38.7 |
| C19 | 151.8 | 151.8 |
| C19=CH2 | 104.5 | 104.5 |
| C20 | 75.4 | 75.4 |
| C21 | 29.5 | 29.5 |
| C22 | 32.0 | 32.0 |
| C23 | 74.9 | 74.9 |
| C24 | 43.4 | 43.4 |
| C25 | 35.9 | 35.9 |
| C25=CH3 | 18.0 | 18.0 |
| C26 | 151.6 | 151.6 |
| C26=CH2 | 104.2 | 104.2 |
| C27 | 73.5 | 73.5 |
| C28 | 36.9 | 36.9 |
| C29 | 71.2 | 71.2 |
| C30 | 76.9 | 77.2 |
| C31 | 36.6 | 36.6 |
| C31=CH3 | 15.1 | 15.1 |
| C32 | 77.5 | 77.4 |
| C33 | 66.3 | 66.3 |
| C34 | 29.1 | 29.1 |
| C35 | 75.0 | 75.1 |
| C36 | 76.2 | 76.2 |

TABLE 5-continued

$^{13}$C NMR DATA OF HALICHONDRIN B (ML1 135.5) AND MINOR 1 (ML1 138.2) (75 MHz in CDCl$_3$, δ in ppm).

| n° CARBON | Hali B | Minor 1 |
|---|---|---|
| C37 | 43.5 | 43.5 |
| C38 | 112.5 | 112.5 |
| C39 | 42.7 | 42.7 |
| C40 | 71.7 | 71.6 |
| C41 | 79.0 | 79.0 |
| C42 | 25.6 | 25.5 |
| C42=CH3 | 17.6 | 17.6 |
| C43 | 36.6 | 36.6 |
| C44 | 97.5 | 97.4 |
| C45 | 36.9 | 36.9 |
| C46 | 25.7 | 25.5 |
| C46=CH3 | 17.8 | 17.8 |
| C47 | 80.2 | 79.4 |
| C48 | 71.7 | 71.7 |
| C49 | 35.9 | 32.0 |
| C50 | 79.8 | 80.8 |
| C51 | 73.0 | 72.6 |
| C52 | 37.2 | 30.6 |
| C53 | 70.4 | 31.0 |
| C54 | 66.9 | 72.2 |
| C55 | | 67.0 |

TABLE 6

$^1$H NMR DATA OF HALICHONDRIN B (ML1 135.5) AND MINOR 2 (ML1 200.5), (300 MHz in CDCl$_3$, δ in ppm).

| n° PROTON | Hali B | Minor 2 |
|---|---|---|
| H2 | 2.35 | 2.35 |
| H2 | 2.60 | 2.62 |
| H3 | 3.86 | 3.88 |
| H4 | 1.75 | 1.74 |
| H4 | 1.37 | 1.40 |
| H5 | 1.35 | 1.38 |
| H5 | 2.08 | 2.08 |
| H6 | 4.34 | 4.33 |
| H7 | 2.94 | 2.95 |
| H8 | 4.33 | 4.33 |
| H9 | 4.04 | 4.05 |
| H10 | 4.20 | 4.20 |
| H11 | 4.60 | 4.60 |
| H12 | 4.68 | 4.69 |
| H13 | 1.94 | 1.93 |
| H13 | 2.15 | 2.15 |
| H15 | 2.18 | 2.16* |
| H15 | 1.62 | 1.60* |
| H16 | 2.16 | 2.15* |
| H16 | 1.42 | 1.38* |
| H17 | 4.10 | 4.10 |
| H18 | 2.26 | 2.24 |
| H18 | 2.80 | 2.80 |
| C19—CH2 | 4.98 | 5.00 |
| C19—CH2 | 4.92 | 4.92 |
| H20 | 4.37 | 4.39 |
| H21 | 1.40 | 1.41 |
| H21 | 1.88 | 1.88 |
| H22 | 1.60 | 1.60 |
| H22 | 1.60 | 1.60 |
| H23 | 3.53 | 3.52 |
| H24 | 1.04 | 1.04 |
| H24 | 1.70 | 1.68 |
| H25 | 2.20 | 2.20 |
| C25—CH3 | 1.07 | 1.06 |
| C26—CH2 | 4.81 | 4.82 |
| C26—CH2 | 4.77 | 4.78 |
| H27 | 3.54 | 3.53 |
| H28 | 2.02 | 2.02 |
| H28 | 1.94 | 1.95 |
| H29 | 4.21 | 4.21 |
| H30 | 4.63 | 4.66 |

TABLE 6-continued

¹H NMR DATA OF HALICHONDRIN B (ML1 135.5) AND MINOR 2 (ML1 200.5), (300 MHz in CDCl₃, δ in ppm).

| n° PROTON | Hali B | Minor 2 |
|---|---|---|
| H31 | 2.04 | 2.03 |
| C31—CH3 | 0.99 | 1.00 |
| H32 | 3.18 | 3.19 |
| H33 | 3.80 | 3.81 |
| H34 | 1.79 | 1.76 |
| H34 | 2.13 | 2.13 |
| H35 | 4.10 | 4.10 |
| H36 | 4.10 | 4.10 |
| H37 | 2.35 | 2.35 |
| H37 | 1.92 | 1.92 |
| H39 | 2.24 | 2.18 |
| H39 | 2.24 | 2.18 |
| H40 | 4.00 | 4.18 |
| H41 | 3.63 | 3.59 |
| H42 | 2.23 | 2.21 |
| C42—CH3 | 0.94 | 0.94 |
| H43 | 1.52 | 1.48 |
| H43 | 1.29 | 1.30 |
| H45 | 1.50 | 1.88 |
| H45 | 1.42 | 2.11 |
| H46 | 2.35 | |
| C46—CH3 | 0.99 | 1.35 |
| H47 | 3.61 | 2.82 |
| H47 | | 1.50 |
| H48 | 4.05 | 4.28 |
| H49 | 2.32 | 4.01 |
| H49 | 1.90 | |
| H50 | 4.08 | 1.74 |
| H50 | | 1.84 |
| H51 | 3.80 | 3.90 |
| H52 | 1.62 | 3.56 |
| H52 | 1.79 | |
| H53 | 4.02 | 3.73 |
| H53 | | 3.73 |
| H54 | 3.54 | |
| H54 | 3.61 | |

*Assignments are tentative

TABLE 7

¹³C NMR DATA OF HALICHONDRIN B (ML1 135.5) AND MINOR 2 (ML1 200.5)* (75 MHz in CDCl₃, δ in ppm).

| n° CARBON | Hali B | Minor 2 |
|---|---|---|
| C1 | 171.2 | |
| C2 | 40.4 | 40.4 |
| C3 | 73.7 | 73.7 |
| C4 | 30.7 | 30.7 |
| C5 | 30.0 | 30.0 |
| C6 | 68.2 | 68.2 |
| C7 | 77.7 | 77.7 |
| C8 | 74.3 | 74.3 |
| C9 | 73.8 | 73.8 |
| C10 | 76.5 | 76.6 |
| C11 | 82.1 | 82.1 |
| C12 | 81.1 | 81.1 |
| C13 | 48.3 | 48.3 |
| C14 | 110.1 | 110.1 |
| C15 | 34.4 | 34.4 |
| C16 | 28.2 | 28.2 |
| C17 | 75.5 | 75.5 |
| C18 | 38.7 | 38.7 |
| C19 | 151.8 | |
| C19═CH2 | 104.5 | 104.0 |
| C20 | 75.4 | 75.4 |
| C21 | 29.5 | 29.5 |
| C22 | 32.0 | 32.0 |
| C23 | 74.9 | 74.9 |
| C24 | 43.4 | 43.4 |
| C25 | 35.9 | 35.9 |
| C25═CH3 | 18.0 | 18.0 |
| C26 | 151.6 | 153.0 |
| C26═CH2 | 104.2 | 103.8 |
| C27 | 73.5 | 73.5 |
| C28 | 36.9 | 36.9 |
| C29 | 71.2 | 71.2 |
| C30 | 76.9 | 77.2 |
| C31 | 36.6 | 36.6 |
| C31═CH3 | 15.1 | 15.1 |
| C32 | 77.5 | 77.4 |
| C33 | 66.3 | 66.3 |
| C34 | 29.1 | 29.1 |
| C35 | 75.0 | 75.1 |
| C36 | 76.2 | 76.2 |
| C37 | 43.5 | 43.5 |
| C38 | 112.5 | 112.5 |
| C39 | 42.7 | 42.7 |
| C40 | 71.7 | 70.9 |
| C41 | 79.0 | 78.6 |
| C42 | 25.6 | 26.1 |
| C42═CH3 | 17.6 | 17.6 |
| C43 | 36.6 | 38.6 |
| C44 | 97.5 | 96.4 |
| C45 | 36.9 | 52.4 |
| C46 | 25.7 | 80.2 |
| C46═CH3 | 17.8 | 25.5 |
| C47 | 80.2 | 36.8 |
| C48 | 71.7 | 75.9 |
| C49 | 35.9 | 81.7 |
| C50 | 79.8 | 35.0 |
| C51 | 73.0 | 71.6 |
| C52 | 37.2 | 73.6 |
| C53 | 70.4 | 65.0 |
| C54 | 66.9 | |
| C55 | | |

*Chemical shifts from HMQC and HMBC experiments

We claim:
1. Halichondrins of the formula:

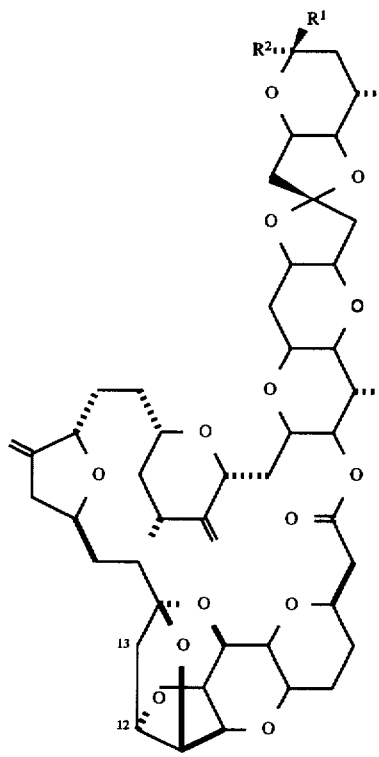

in which $R^1$ and $R^2$ together represent a spiro attached group selected from the following:

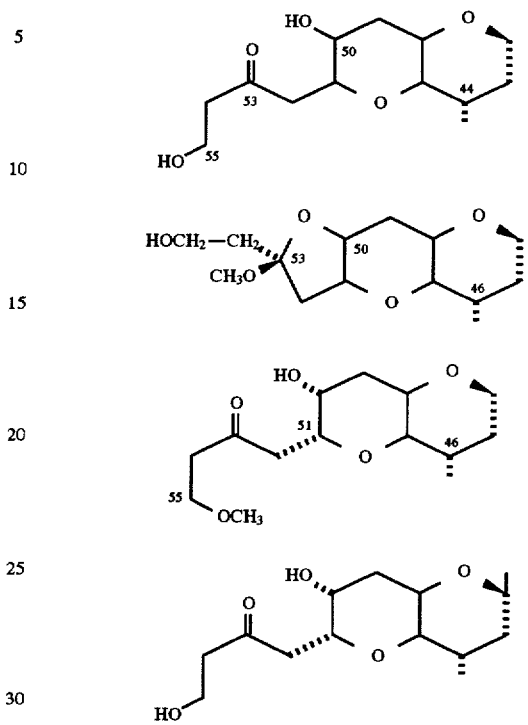

2. Isohomohalichondrin B. of the formula:

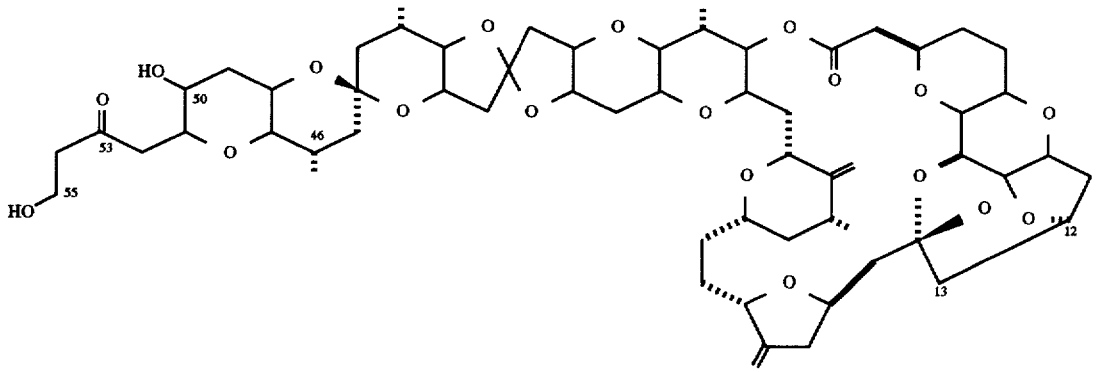

3. A pharmaceutical composition comprising a halichondrin according to claim 1. together with a pharmaceutical carrier or diluent.

4. A pharmaceutical composition comprising a halichondrin according to claim 2. together with a pharmaceutical carrier or diluent.

* * * * *